United States Patent [19]

Rogers

[11] 4,288,298

[45] Sep. 8, 1981

[54] METHOD AND APPARATUS FOR ELECTROPLATING OR ELECTROFORMING METAL OBJECTS

[76] Inventor: Olbert W. Rogers, 70 Gymea Bay Rd., Gymea, New South Wales, Australia, 2227

[21] Appl. No.: 129,293

[22] Filed: Mar. 11, 1980

[30] Foreign Application Priority Data

Mar. 14, 1979 [AU] Australia ............................ PD8025

[51] Int. Cl.³ .................. C25D 1/00; C25D 5/00; C25D 17/06; C25D 17/10
[52] U.S. Cl. ................................... 204/4; 204/23; 204/228; 204/297 W
[58] Field of Search .............. 204/3, 4, 14 R, 15, 204/228, 231, DIG. 7, 297 W, 285, 283, 23

[56] References Cited

U.S. PATENT DOCUMENTS

| | | | |
|---|---|---|---|
| 902,892 | 11/1908 | Lutz | 204/228 |
| 1,870,958 | 8/1932 | Monroe | 204/228 |
| 2,861,936 | 11/1958 | Colasanto | 204/297 W |
| 2,916,431 | 12/1959 | O'Connor | 204/297 W |
| 3,043,767 | 7/1962 | Tobey | 204/297 W |
| 3,553,096 | 1/1971 | Coir | 204/297 W |

FOREIGN PATENT DOCUMENTS 574316 4/1933 Fed. Rep. of Germany ........ 204/15

Primary Examiner—T. M. Tufariello
Attorney, Agent, or Firm—Ladas & Parry

[57] ABSTRACT

The invention relates primary to the field of dentistry, particularly to the formation of dental crowns, and provides an apparatus for use in electrodeposition of a metal onto a plurality of substrates, which comprises a retainer for an electrolyte, a first electrode member having means for supporting said plurality of substrates within said retainer, a second electrode member having a plurality of support zones for supporting pieces of said metal within said retainer, connecting means for mounting the first electrode member in the retainer and intended for connecting the first electrode member to one pole of a direct current supply, mounting means for mounting the second electrode member in the retainer, and means for making selective connection of one or more of the electrode support zones to the other pole of the direct current supply.

Generally, each substrate is a tooth replica having a conductive outer coating and mounted on a metal former for screwing into the first electrode member. Also, each support zone is preferable a metal basket for containing a piece of the depositing metal.

5 Claims, 10 Drawing Figures

METHOD AND APPARATUS FOR ELECTROPLATING OR ELECTROFORMING METAL OBJECTS

FIELD OF THE INVENTION

This invention relates to an apparatus for use in electroplating a metallic substrate or for use in electroforming a hollow metallic object.

The invention has particular though non-exclusive application in the construction of dental implants or dental crowns and, for explanatory purposes only, is herein described in such context. Thus, in the formation of dental implants, the apparatus may be employed for electrolytically etching a substrate and then electroplating a metal coating onto the substrate, which subsequently is to be coated with a dental porcelain. Such a plating process is proposed for the purpose of providing a bond-aiding interface between a high strength alloy substrate and the porcelain. In the context of electroforming, the apparatus may be employed in the formation of a hollow matrix upon which a dental porcelain is subsequently to be deposited for the purpose of producing a dental crown. However, it is to be understood that the apparatus need not be employed solely for electroplating or electroforming objects for use in dentistry, and that the apparatus may be used in the plating or formation of other objects.

DESCRIPTION OF THE PRIOR ART

Electro-deposition techniques, including both electroplating and electroforming techniques, are in general widely understood and documented. However, to the inventor's knowledge, no previous apparatus has been proposed which is suited to the specialised needs which exist in the construction of dental implants and dental crowns. For such purposes, an electro-deposition apparatus should be capable of predictable performance in electro-depositing metal onto either a small number or a large number of substrates, so that the demands of varying work loads may be met. At the same time, the apparatus should not be so operationally complex as to tax the ability of users who are not specialists in the electro deposition field. These are seemingly incompatible requirements which, along with other requirements, the present invention seeks to meet.

SUMMARY OF THE INVENTION

Thus, the present invention provides an apparatus for use in electrodeposition of a metal onto a plurality of substrates, which comprises a retainer for an electrolyte, a first electrode member having means for supporting said plurality of substrates within said retainer, a second electrode member having a plurality of support zones for supporting pieces of said metal within said retainer, connecting means for mounting the first electrode member in the retainer and intended for connecting the first electrode member to one pole of a direct current supply, mounting means for mounting the second electrode member in the retainer, and means for making selective connection of one or more of the electrode support zones to the other pole of the direct current supply.

Preferably, each of the support zones comprises a metal basket like pocket which is mounted to the second electrode member and which is connected by an electrical conductor to a terminal connector. The terminal connector may comprise the above stated means for mounting the second electrode member in the retainer. The second electrode member preferably comprises a plastics material panel which mounts the pockets and in which the electrical conductors which connect with the pockets are located.

The first electrode member preferably comprises a metal plate which is sandwiched between two plastics material plates, with one of the two plastics material plates being formed with an array of apertures. The apertures are provided for receiving a projecting portion of the substrates and, when each substrate is fitted to the first electrode member, the projecting portion engages with the metal plate. Most preferably, the metal plate is also formed with an array of apertures which align with corresponding apertures in the plastics material plate, and the various apertures are threaded to receive a screw projection of the substrate. Then, a sheet of resilient material such as neoprene is also sandwiched between the plastics material plates, as a backing for the metal plate.

With the construction as above defined, one or more substrates may be mounted to the first electrode member and, according to the number of substrates so mounted, one or more of the pieces of the depositing metal may be mounted to the second electrode member. Then, only those support zones which carry a depositing metal will need be connected (e.g., as anodes) to said other pole of the direct current supply. This permits standardization of the size of the pieces of depositing metal to be provided for use with the apparatus, and it allows for the provision of simple operating instructions for the apparatus. Thus, with predetermination of the approximate surface area of the substrates and appropriate control of agitation and temperature of the electrolyte, selection may readily be made of the current required to give a current density (amps/dm$^2$) to provide for a controlled rate of deposition and ion replenishment. When less than the maximum possible number of substrates are mounted to the first electrode member, the unoccupied apertures in the member may be plugged with non-conductive material plugs to prevent wasteful deposition of material onto the metal portion of the first electrode member.

Each substrate may comprise a unitary element, for example a metal element to be electroplated, or it may comprise a composite element. In the latter case, the substrate may comprise a metal post which is arranged to be mounted to the first electrode member and a moulding onto which electro-deposition is to be made. The moulding may be formed from a non-conductive material, provided that a conductive coating (e.g., a metallic paint) is applied to the material and extended over the metal post. By use of the latter technique, electroforming of metal matrices may be achieved.

BRIEF DESCRIPTION OF THE DRAWINGS

The invention will be more fully understood from the following description of a preferred embodiment of an electro-deposition apparatus. The description is given with reference to the accompanying drawings wherein.

DETAILED DESCRIPTION OF THE DRAWINGS

Figure 1:
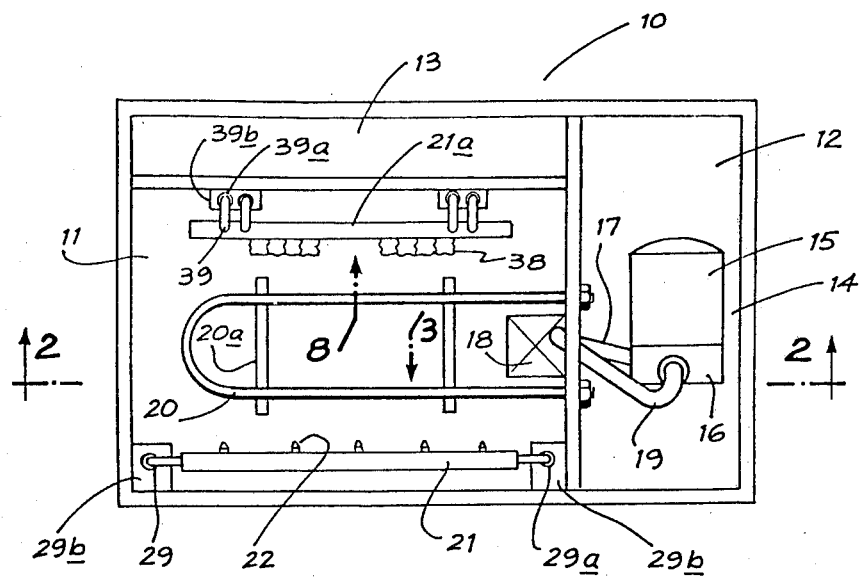
FIG. 1 shows a plan view of a tank portion of the apparatus, including a retainer for electrolyte and associated equipment.

The apparatus as shown in the drawings is suitable for use in electroforming hollow metal articles such as gold matrices for dental crowns. In the absence of a suitable electroforming apparatus, such matrices previously have been hand modelled from platinum. In use of the apparatus, a number of gold matrices are electro-formed to a thickness of approximately 200 $\mu$m upon male moulds which are formed from artificial stone. Having electroformed the matrices, they are removed from the apparatus, the artificial stone is removed from the matrices and the matrices are covered with an appropriately configured layer of dental porcelain. The invention is not concerned so much with the production of the complete dental crowns, but with the apparatus for use in electroforming matrices for the crowns.

Figure 2:
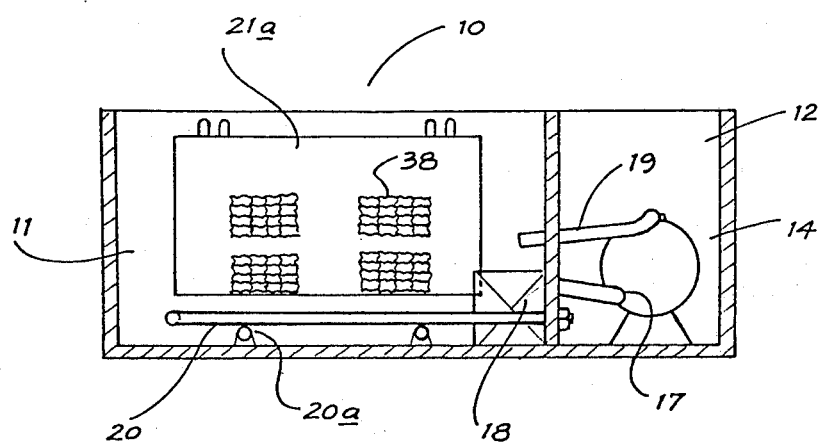
FIG. 2 shows a sectional elevation view of the tank portion, as viewed in the direction of section plane 2—2 of FIG. 1.

As shown in FIGS. 1 and 2 of the drawings, the apparatus comprises a plastics material tank 10 which is formed with three compartments 11, 12 and 13, the compartments being defined by plastics material walls. The first compartment 11 comprises a retainer for electrolyte or, stated in other words, an electroforming bath. The second compartment 12 contains a motor/pump arrangement 14 for recirculating the electrolyte through the first compartment, and the third compartment 13 provides a storage zone for ancilliary equipment to be used in the apparatus. The second and third compartments provide collection zones for any electrolyte that may leak through imperfectly sealed apertures which interconnect the various compartments and through which electrical wiring is passed.

The motor/pump arrangement 14 comprises an electric motor 15 and a magnetic induction impeller type pump 16. The pump includes a suction line 17 which projects into the retainer 11, adjacent the base of the retainer, and couples with a filter 18. The pump further includes a return line 19 which also projects into the retainer but at a higher level than the suction line. The return line 19 is orientated at an angle so that returned electrolyte is directed towards a second electrode member 21a to which reference is hereinafter made. The pump has a capacity of 7 liters per minute and, in addition to its normal function of recirculating and hence agitating the electrolyte, the pump may be used for draining the retainer of electrolyte by diverting the return line to a reservoir.

The tank 10 would normally be fitted with a cover (not shown) to reduce losses of the electrolyte due to evaporation.

For the purpose of electroforming gold, the electrolyte may be constituted by a solution having the following composition:

TABLE 1

| ELECTROPLATING SOLUTION | |
|---|---|
| SOLUTION | GRAMME |
| Potassium gold cyanide | 14.1 |
| Potassium cyanide | 18.3 |
| Potassium carbonate | 14.1 |
| Boric acid | 11.4 |
| Distilled water | Quantity to make 1 liter |

In addition to the filter 18, the compartment 11 contains a heater element 20, a removably mounted first electrode member 21 and a removably mounted second electrode member 21a.

The heater element 20 comprises a fused alumina heater, to which electrical connections are made via the second compartment 12, and the heater is supported upon and spaced from the compartment base by fused alumina supports 20a. The supports 20a are tubular to permit the through flow of electrolyte as a cooling agent.

Figure 4:
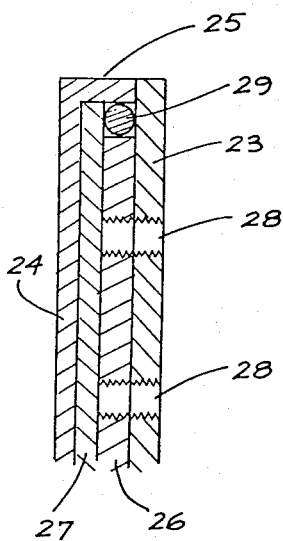
FIG. 4 shows a detailed sectional elevation view of a portion of the first electrode member, the view being taken in the direction of section plane 4—4 shown in FIG. 3
Figure 5:
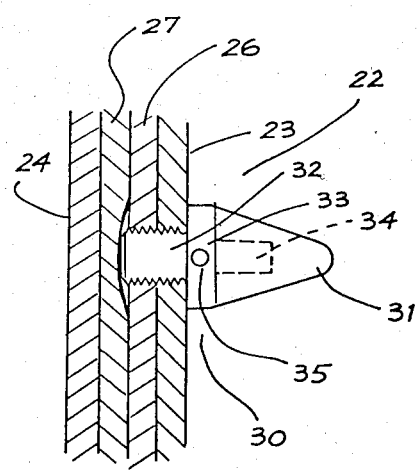
FIG. 5 shows a detailed sectional elevation view of a portion of the first electrode member with a substrate mounted thereto.

The first electrode member 21 provides a support for substrates 22 upon which gold matrices are to be electroformed. The construction of the electrode member 21 is illustrated in detail in FIGS. 3 to 5, to which reference is now made.

As shown, the first electrode member 21 comprises a plastics material first panel 23, and a plastics material second panel 24 which is formed with a peripheral lip 25. Also, sandwiched between the two panels are a stainless steel plate 26 and a synthetic rubber backing mat 27.

The first panel 23 and the metal plate 26 are both formed with an array of twenty threaded apertures 28 into which the substrates 22 can be screwed. When screwed into the apertures, the substrates seal against the front face of the panel 23 and make electrically-conductive contact with the metal panel 26.

Figure 3:
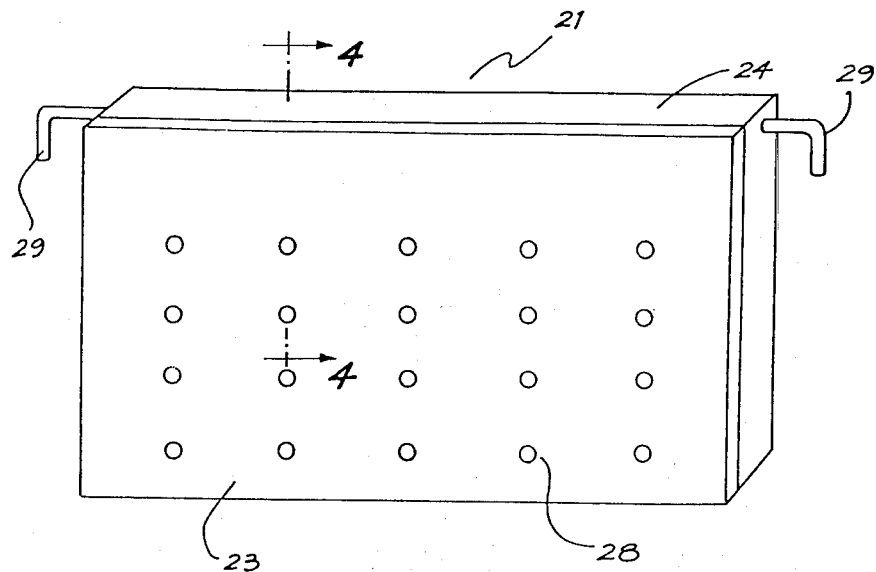
FIG. 3 shows a perspective view of a first electrode member of the apparatus, as viewed in the direction of arrow 3 in FIG. 1.

A stainless steel rod 29 connects with and extends along the top edge of the metal plate 26, the rod then projecting outwardly from both ends of the electrode member and then downwardly as shown in FIG. 3. The metal rod provides means by which the electrode member 20 is located in the compartment 11 and by which the plate 26 is connected as a cathode to a direct current supply. Thus, the downwardly projecting portions of the metal rod are removably located in metal contact sleeve terminals 29a which are fixed in plastics material terminal blocks 29b, as shown in FIG. 1.

The substrate 22 comprises a stainless steel post 30 and a moulding 31 which is formed as a replica of a tooth stump to which a porcelain encased matrix is to be fitted. The moulding 31 is produced from artificial stone (Hydrocal), is obtained from a impression which is taken from a patient's tooth stump that is to be capped, and is mounted to the post 30.

The post 30 comprises a threaded shank or projection 32 which locates in one or other of the apertures 28, a flange portion 33 and a peg 34 which locates in the moulding 31. Two diametrically aligned holes 35 are provided in the flange portion 33 of the post to permit the substrate to be held and manipulated by a hand-held pronged implement 36 (FIGS. 6 and 7).

Figure 6:
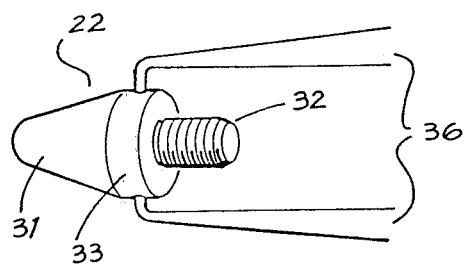
FIGS. 6 and 7 illustrate a method of holding the substrate prior to mounting it to the first electrode member.
Figure 7:
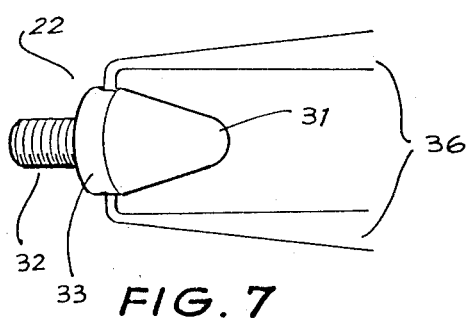

Following formation of the artificial stone moulding 31 on the post 30, the complete substrate is held as shown in FIG. 6 and the moulding is coated with a conductive paint (e.g., Degussa 200 conducting silver paint), with care being taken to ensure that the paint covers the entire moulding and extends over the flange portion 33 of the post. Thereafter, the flange portion 33 of the post is further coated with a non-conductive coating, so as to avoid wasteful electro-deposition of gold onto any surface other than that of the moulding 31. Finally, without touching the surface of the moulding 31, the substrate is turned to the position shown in FIG. 7 and, using the implement 36, the substrate is screwed into the electrode member 21.

If less than twenty substrates are to be treated during any one electroforming operation, the remaining apertures 28 in the electrode member are sealed with plastics material plugs.

Figure 8:
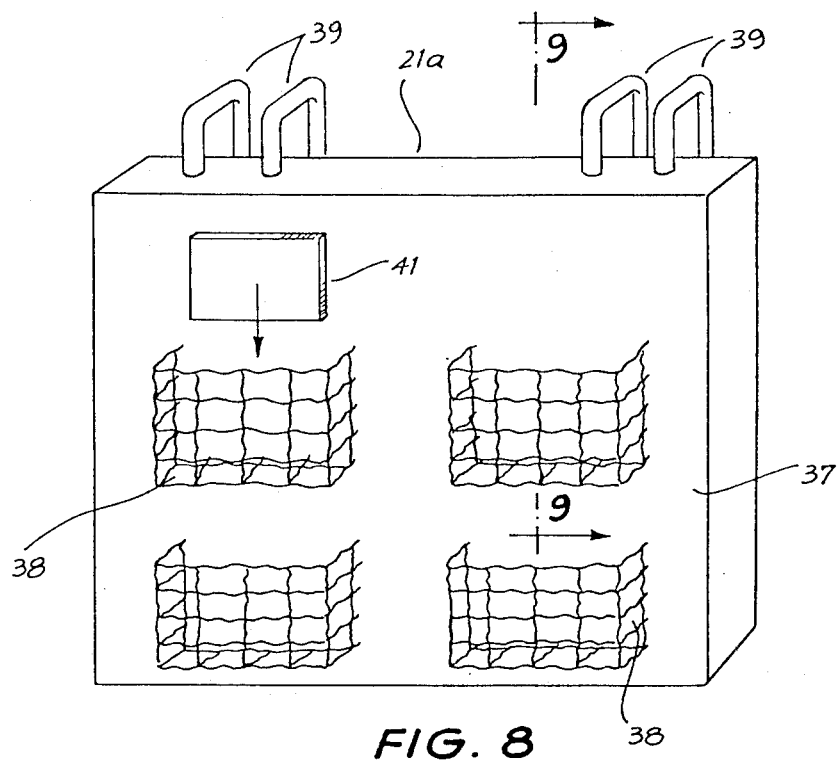
FIG. 8 shows a perspective view of a second electrode member of the apparatus, as viewed in the direction of arrow 8 in FIG. 1.
Figure 9:
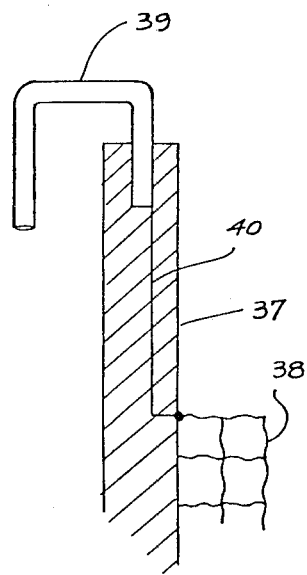
FIG. 9 shows a detailed sectional view of the second electrode member, the view being taken in the direction of section plane 9—9 shown in FIG. 8.

Reference is now made to FIGS. 8 and 9 of the drawings which detail the construction of the second electrode member 21a. This comprises a plastics material panel 37 to which are mounted four stainless steel basket-like pockets 38. Each pocket is formed from stainless steel wire mesh and is connected to a respective one of four inverted U-shaped stainless steel conductor rods 39 by an internal conductor 40. The conductor rods 39 serve to locate the electrode member 21a in the compartment 11 and provide terminal connectors through which the baskets (or, more correctly, gold contents of the basket) are connected as anodes to a direct current supply. Thus, as shown in FIG. 1, each conductor rod 39 is removably located in a stainless steel terminal sleeve 39a which is in turn located in a plastics material terminal block 39b.

In operation of the apparatus, a gold sheet 41 is located in one or more of the pockets 38, depending upon the number of substrates upon which electro-deposition is to be made, and, when electrical current is passed through the electrolyte from the anode to the cathode, the gold sheet is progressively reduced as ions from the electrolyte are depleted and replaced from the anode material.

The gold sheet 41 which is placed in the each pocket has a thickness which is approximately equal to or greater than that of the gold coating to be deposited on the substrates and it has a surface area which is approximately doubled that of one row of the substrates. The gold sheet 41 which is located in each pocket may be regarded as serving one row only of substrates and, if some rows of the apertures 28 in the first electrode member 21 are unoccupied by substrates, an electrical connection is not made to appropriate ones of the pockets 38. This procedure is more fully described later in the specification with reference to FIG. 10.

If the total thickness of gold deposit on each substrate is to be 200 μm and the total affective area of one row of substrates is 1.0 cm.², then each gold sheet will have a thickness of 250 μm and a surface area of 2.0 cm.².

Maintenance of a required surface area of the anode (i.e., depositing material) 41 is important for the prevention of polarisation when rapid electrodeposition procedures are involved. It has been found that current concentration at the edges of the gold sheets 41 causes irregular dissolution and area control is (in other forms of apparatus) difficult to maintain. However, in the apparatus of the present invention, as dissolution occurs behind the mesh pockets 38, a reduction of the surface area can readily be seen and new pieces of the depositing metal can be placed in the pockets as and when required.

Figure 10:
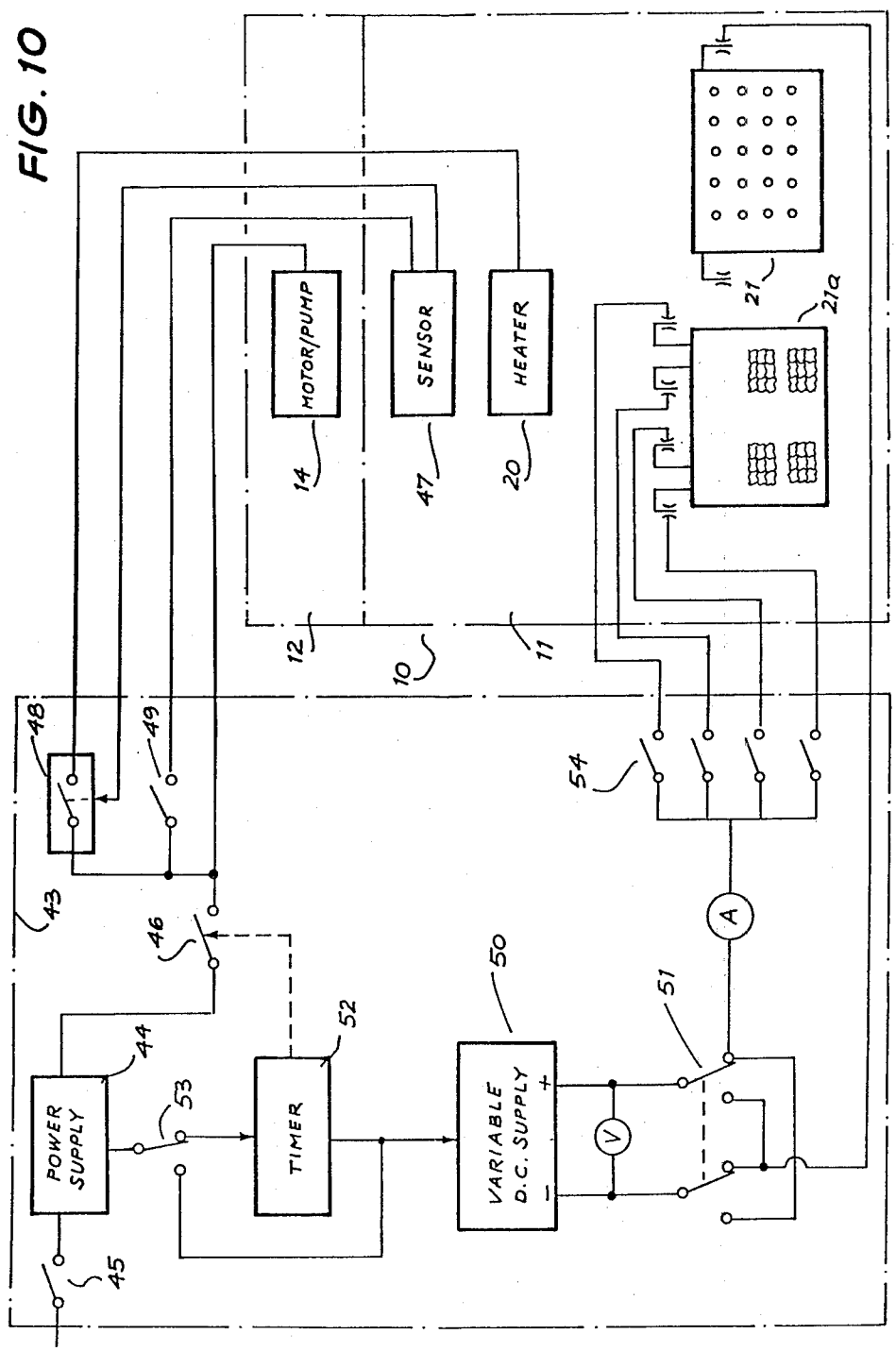
FIG. 10 shows a schematic circuit of electrical power supply and control circuitry for the apparatus.

Electrical circuitry for the above described apparatus is shown in schematic form in FIG. 10 of the drawings. Most of the electrical circuit elements which are shown in FIG. 10 are housed in a control unit 43 which is separate from the retainer 10 but which is connected to the retainer by electrical cables.

The control unit comprises a power supply 44 which is connectable via a main switch 45 to a mains distribution system. One output from the power supply is applied to the motor/pump 14 via a switch 46 and a connection is also made to the heater 20 by way of a sensor 47. Neither the heater nor the sensor can be energised until such time as the motor/pump unit 14 is energised, to avoid localised overheating and degradation of the electrolyte, and the heater may be energised, by way of switch 48, only after the sensor has been activated by way of a switch 49. The sensor operates as a control unit for the heater and cycles the heater in accordance with the prevailing temperature conditions of the electrolyte.

A further output from the power supply 44 is connected as an input to a variable direct current supply 50. The positive and negative output terminals of the direct current supply are connected, respectively, to the anode and cathode in the compartment 11. Two-position switches 51 are located in the positive and negative output lines from the DC supply to permit polarity reversal of the anode and cathode, so that reverse plating may be effected.

Although not shown in the drawings, the power supply 50 includes a (voltage) step-down transformer, a rectifier network and means for providing a current supply which can be maintained substantially constant at a selected level. Such means may comprise a rheostat or, preferably a controlled semiconductor device such as a power transistor or a silicon controlled rectifier. When a semiconductor current level control device is employed, current level selector switches may be incorporated in the power supply circuit to facilitate convenient operation.

A voltmeter (V) is connected across the DC supply output and an ammeter (A) is connected in the positive line of the DC supply for the purpose of measuring anode current. The anode current is normally regulated to provide a current density of 3.2 amps/dm².

A timer 52 is located in circuit with the DC supply for the purpose of controlling an electroforming time cycle, and a switch 53 is located in circuit with the timer for the purpose of isolating the timer if manual control of the apparatus is required. Also, the timer 52 may be employed to actuate the switch 46, so that the entire apparatus may be switched-off when a duty cycle is complete.

The negative supply line from the DC supply is connected to both of the connectors 29 of the first support member 21, and the positive supply line from the DC supply is separately connected to each of the connectors 39 of the second support member 21a by way of four selector switches 54. Closing of one or other or all of the switches 54 determines the number of anodes which are to be connected in circuit during operation of the apparatus.

I claim:

1. An apparatus for use in electrodeposition of a metal onto a chosen variable number of substrates, which comprises
   a retainer for an electrolyte,
   a first electrode member having means for supporting said plurality of substrates within said retainer,
   a second electrode member comprising a non-conductive panel having mounted thereon a plurality of metal baskets, each metal basket being for containing in electrical connection therewith a piece of said metal to be electrodeposited,
   connecting means for mounting the first electrode member in the retainer and intended for connecting the first electrode member to one pole of a direct current supply,
   mounting means for mounting the second electrode member in the retainer, and
   means for making selective connection of a number of the metal baskets to the other pole of the direct current supply, the remaining baskets not being connected to the supply.

2. An apparatus according to claim 1, wherein the second electrode member comprises a plastics panel having mounted on one face thereof of plurality of metal basket-like pockets.

3. An apparatus according to claim 1, wherein the first electrode member comprises a metal plate sandwiched between two plastics plates, the metal plate having an array of screw-threaded bores for receiving screw-threaded projecting portions of said substrates, the plastics plate on one side of the metal plate having a corresponding array of aligned apertures and a sheet of resilient material being sandwiched between the other plastics plate and the metal plate.

4. An apparatus according to claim 1 for the production of dental caps, which further comprises a plurality of posts, each post having a metallic portion for making electrical contact with the first electrode member, each post being adapted to receive a tooth replica onto which said metal is to be electrodeposited to form a cap, the size of said baskets being such that the maximum total area of metal that may be contained therein is greater than the maximum total surface area of the tooth replicas which may be received on said posts.

5. A method for electrodepositing metal onto a plurality of substrates using the apparatus of claim 1, which comprises
   providing an electrolyte solution in the retainer,
   supporting a plurality of substrates on the first electrode member within the electrolyte,
   supporting a number of pieces of said metal within the electrolyte in baskets of the second electrode member, the number being determined in dependence on the number of substrates on the first electrode,
   connecting said pieces of metal in the baskets of the second electrode member to one pole of a direct current supply,
   connecting the substrates on the first electrode to the other pole of the direct current supply, and
   passing an electric current through the electrolyte.

* * * * *